United States Patent
Sato et al.

(10) Patent No.: US 11,959,123 B2
(45) Date of Patent: Apr. 16, 2024

(54) METHOD FOR QUANTIFYING DIAMINOPIMELIC ACID-CONTAINING BACTERIA

(71) Applicant: SUNTORY HOLDINGS LIMITED, Osaka (JP)

(72) Inventors: Yosuke Sato, Kyoto (JP); Naoki Kasajima, Kyoto (JP); Toshihiko Fukuda, Kyoto (JP); Masayuki Ida, Kyoto (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 223 days.

(21) Appl. No.: 17/439,901

(22) PCT Filed: Mar. 9, 2020

(86) PCT No.: PCT/JP2020/009936
§ 371 (c)(1),
(2) Date: Sep. 16, 2021

(87) PCT Pub. No.: WO2020/189363
PCT Pub. Date: Sep. 24, 2020

(65) Prior Publication Data
US 2022/0186279 A1 Jun. 16, 2022

(30) Foreign Application Priority Data
Mar. 19, 2019 (JP) .................................. 2019-051664

(51) Int. Cl.
*C12Q 1/06* (2006.01)
*C12N 1/20* (2006.01)

(52) U.S. Cl.
CPC ............... *C12Q 1/06* (2013.01); *C12N 1/205* (2021.05)

(58) Field of Classification Search
CPC .............. C12N 1/205; C12R 2001/225; C12R 2001/25; C12Q 1/06
See application file for complete search history.

(56) References Cited

U.S. PATENT DOCUMENTS

| 2011/0104746 A1 | 5/2011 | Muto |
| 2012/0156760 A1 | 6/2012 | Izumo et al. |

FOREIGN PATENT DOCUMENTS

| JP | 2017-226635 A | 12/2017 | |
| JP | 2018-201531 A | 12/2018 | |
| WO | 2009/157316 A1 | 12/2009 | |
| WO | 2010/110045 A1 | 9/2010 | |
| WO | WO-2010110045 A1 * | 9/2010 | ........... A23L 1/3014 |

OTHER PUBLICATIONS

El-Shazly K, Hungate RE. Method for measuring diaminopimelic acid in total rumen contents and its application to the estimation of bacterial growth. Appl Microbiol. Jan. 1966; 14(1):27-30. doi: 10.1128/am.14.1.27-30.1966. PMID: 5914492; PMCID: PMC546612. (Year: 1965).*
Wells JE, Russell JB. Why do many ruminal bacteria die and lyse so quickly? J Dairy Sci. Aug. 1996;79(8):1487-95. doi: 10.3168/jds.S0022-0302(96)76508-6. PMID: 8880474. (Year: 1996).*
Marconi et al., "Rapid Detection of meso-Diaminopimelic Acid in Lactic Acid Bacteria by Microwave Cell Wall Hydrolysis", J. Agric. Food Chem. 2000, vol. 48, pp. 3348-3351, cited in Search Report and Written Opinion dated Dec. 19, 2022. (4 pages).
Robinson et al., "Critical evaluation of diaminopimelic acid and ribonucleic acid as marker to estimate rumen pools and duodenal flows of bacterial and protozoal nitrogen", Canadian Journal of Animal Science, 1996, pp. 587-597, cited in Search Report and Written Opinion dated Dec. 19, 2022. (11 pages).

* cited by examiner

*Primary Examiner* — Suzanne M Noakes
*Assistant Examiner* — Jae W Lee
(74) *Attorney, Agent, or Firm* — WHDA, LLP

(57) ABSTRACT

The present invention aims to provide a novel method that can quantify diaminopimelic acid-containing bacteria in a test sample. The present invention relates to a method of quantifying diaminopimelic acid-containing bacteria in a test sample, including a step of quantifying the diaminopimelic acid-containing bacteria, using, as an index, the amount of diaminopimelic acid derived from the diaminopimelic acid-containing bacteria in the test sample.

5 Claims, 2 Drawing Sheets

METHOD FOR QUANTIFYING DIAMINOPIMELIC ACID-CONTAINING BACTERIA

TECHNICAL FIELD

The present invention relates to a method of quantifying diaminopimelic acid-containing bacteria in a test sample.

BACKGROUND ART

Lactic acid bacteria and the like are added to some foods in response to an increase in health consciousness and the like. Such bacteria may be added in the form of living bacteria (viable bacteria) or killed bacteria (dead bacteria). For example, when bacteria such as lactic acid bacteria are added as a functional ingredient to foods with functional claims or the like, it is important to determine the viable bacterial number and the dead bacterial number in such products.

Examples of methods of quantifying viable bacteria in a sample include a method of culturing a sample in an agar medium and then enumerating colonies (culture method). For example, Patent Literature 1 discloses an enumeration method of microorganisms in a specimen, the method including: a step of preparing a suspension for the specimen using a dilution for suspension; and a step of measuring a viable cell count of the microorganisms in the suspension. According to Patent Literature 1, the viable cell count of the microorganisms in the suspension can be determined by the culture method in which microorganisms are cultured in an agar medium.

In the case of dead bacteria powder or a product containing dead bacteria powder, since the added bacteria are dead bacteria, the culture method cannot be used to determine the bacterial count. In the case of a sample for which the culture method cannot be used to determine the bacterial count, the total bacterial count is determined. Use of a microscope is a mainstream method for determining the total bacterial count. A method such as DAPI (fluorescent) staining is known as a typical method. In this method, a sample solution obtained by suspending a sample in diluted water is viewed under a microscope to observe the cell shape and enumerate the cells to determine the bacterial count. In the case of DAPI staining, no distinction can be made between dead bacteria and viable bacteria, so that the determined result is treated as the total bacterial count (total number of bacteria).

CITATION LIST

Patent Literature

Patent Literature 1: WO 2009/157316

SUMMARY OF INVENTION

Technical Problem

Some lactic acid bacteria contain diaminopimelic acid (hereinafter also referred to as "DAP") in cell walls. Such lactic acid bacteria containing diaminopimelic acid are also added to some foods and the like. However, no studies have been made on methods of quantifying diaminopimelic acid-containing bacteria in a test sample.

In the case of a test sample that contains DAP-free bacteria in addition to DAP-containing bacteria, the DAP-containing bacteria can be quantified by the culture method as described above if, for example, the DAP-containing bacteria are viable bacteria and the DAP-free bacteria are dead bacteria. In the case of a test sample that contains DAP-containing bacteria and DAP-free bacteria in which both the DAP-containing bacteria and the DAP-free bacteria are viable bacteria, presumably, the DAP-containing bacteria can be quantified by culturing the sample, if possible, under conditions in which only the DAP-containing bacteria can be selectively cultured, and enumerating the resulting colonies.

The culture method cannot be used to determine the number of DAP-containing bacteria in a test sample that contains the DAP-containing bacteria and DAP-free bacteria, in the case where the DAP-containing bacteria are viable bacteria but cannot be selectively cultured against the DAP-free bacteria or in the case where the DAP-containing bacteria are dead bacteria. For example, in the case where the DAP-containing bacteria are dead bacteria and the DAP-free bacteria are viable bacteria, presumably, the number of dead DAP-containing bacteria is determined by subtracting the viable bacteria count from the total bacterial count in the test sample. However, the viable bacterial count and the total bacterial count are determined by different methods. No studies have been made on methods that can selectively quantify DAP-containing bacteria in a test sample that contains the DAP-containing bacteria and DAP-free bacteria, regardless of whether the DAP-containing bacteria are dead bacteria or viable bacteria.

The present invention aims to provide a novel method that can quantify diaminopimelic acid-containing bacteria in a test sample.

Solution to Problem

As a result of extensive studies to solve the above problems, the present inventors found that the amount of diaminopimelic acid derived from lactic acid bacteria containing diaminopimelic acid is highly correlated with the bacterial count of the lactic acid bacteria and that the diaminopimelic acid can be used as an index for quantification of diaminopimelic acid-containing bacteria.

Specifically, the present invention relates to the following analysis methods.

(1) A method of quantifying diaminopimelic acid-containing bacteria in a test sample, including a step of quantifying the diaminopimelic acid-containing bacteria, using, as an index, an amount of diaminopimelic acid derived from the diaminopimelic acid-containing bacteria in the test sample.

(2) The method according to (1) above, wherein the test sample contains diaminopimelic acid-free bacteria.

(3) The method according to (1) or (2) above, wherein the diaminopimelic acid-containing bacteria are dead bacteria.

(4) The method according to any one of (1) to (3) above, wherein the diaminopimelic acid-containing bacteria include at least one type of lactic acid bacteria selected from the group consisting of *Lactobacillus pentosus, Lactobacillus plantarum, Lactobacillus paraplantarum, Lactobacillus fabifermentans, Lactobacillus vaccinostercus, Lactobacillus hokkaidonensis, Lactobacillus oligofermentans, Lactobacillus suebicus, Lactobacillus mali*, and *Lactobacillus divergens*.

(5) The method according to any one of (1) to (4) above, wherein the diaminopimelic acid-containing bacteria are of *Lactobacillus pentosus*.

Advantageous Effects of Invention

The present invention can provide a novel method that can quantify diaminopimelic acid-containing bacteria in a test sample. Use of the quantification method of the present invention enables selective quantification of diaminopimelic acid-containing bacteria in a test sample, even when, for example, the test sample contains diaminopimelic acid-free bacteria in addition to the diaminopimelic acid-containing bacteria. The quantification method of the present invention is useful, for example, for quantifying diaminopimelic acid-containing bacteria in foods, pharmaceuticals, and the like, and in controlling the quality of products containing the bacteria.

DESCRIPTION OF EMBODIMENTS

DESCRIPTION OF EMBODIMENTS

Figure 1:
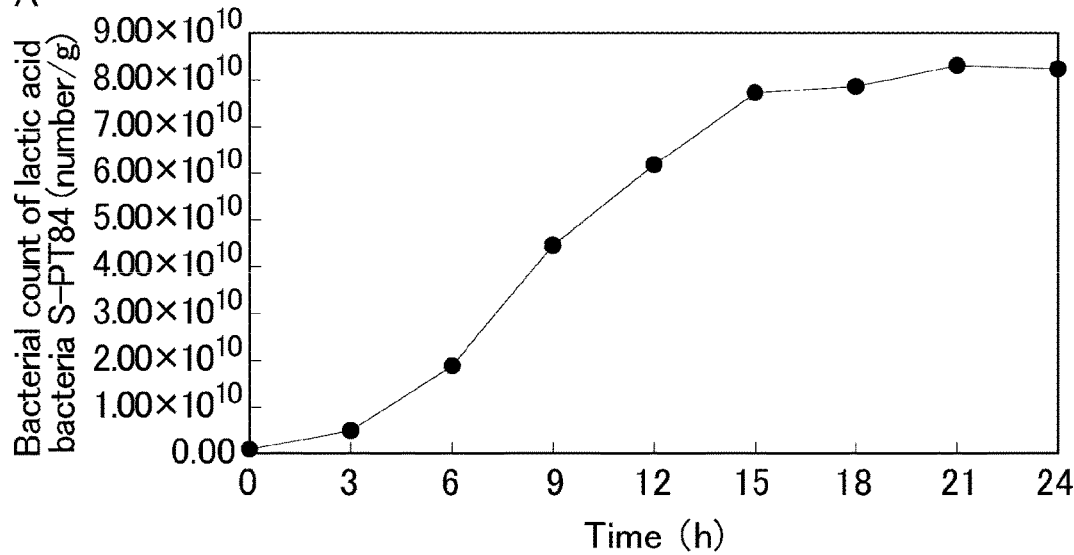
FIG. 1A is a graph showing culture time-dependent changes in the bacterial count of lactic acid bacteria S-PT84.
FIG. 1B is a graph showing culture time-dependent changes in the amount of diaminopimelic acid.
Figure 1:
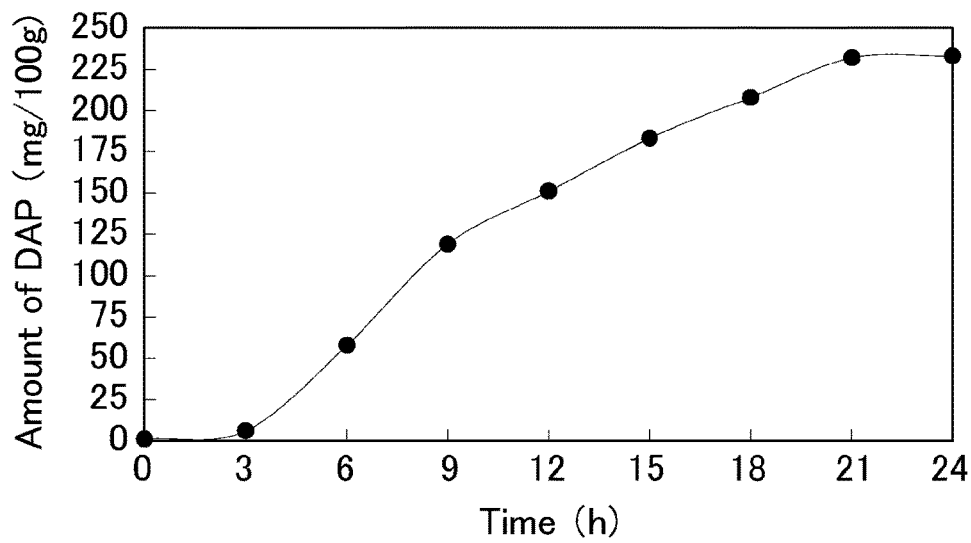

The bacteria quantification method of the present invention is a method of quantifying diaminopimelic acid-containing bacteria in a test sample, including a step of quantifying the diaminopimelic acid-containing bacteria, using, as an index, the amount of diaminopimelic acid derived from the diaminopimelic acid-containing bacteria in the test sample.

The test sample in the present invention usually contains diaminopimelic acid-containing bacteria.

Herein, the diaminopimelic acid (DAP) refers to 2,6-diaminopimelic acid.

Examples of the diaminopimelic acid-containing bacteria include lactic acid bacteria containing diaminopimelic acid in structural components of cell walls, such as *Lactobacillus pentosus*, *Lactobacillus plantarum*, *Lactobacillus paraplantarum*, *Lactobacillus fabifermentans*, *Lactobacillus vaccinostercus*, *Lactobacillus hokkaidonensis*, *Lactobacillus oligofermentans*, *Lactobacillus suebicus*, *Lactobacillus mali*, and *Lactobacillus divergens*.

The diaminopimelic acid-containing bacteria may include only one type or two or more types, but preferably include only one type. In one embodiment of the present invention, preferably, the diaminopimelic acid-containing bacteria are of *Lactobacillus pentosus*.

The diaminopimelic acid-containing bacteria may be viable bacteria or dead bacteria. The amount of diaminopimelic acid derived from the diaminopimelic acid-containing bacteria in the test sample correlates with the number of the bacteria, so that the bacterial count of the diaminopimelic acid-containing bacteria can be determined (the number of bacteria can be quantified) using the amount of diaminopimelic acid as an index, and the bacteria can be quantified. The quantification method of the present invention is useful for determining the number of diaminopimelic acid-containing bacteria. The bacteria quantification method of the present invention uses the amount of diaminopimelic acid derived from diaminopimelic acid-containing bacteria in a test sample as an index to quantify the diaminopimelic acid-containing bacteria. Thus, the method can quantify the bacteria, regardless of whether the bacteria are viable bacteria or dead bacteria.

The test sample may contain diaminopimelic acid-free bacteria. The method of the present invention is useful for quantifying diaminopimelic acid-containing bacteria in a test sample that contains the diaminopimelic acid-containing bacteria and diaminopimelic acid-free bacteria.

The diaminopimelic acid-free bacteria are not limited. Examples of the diaminopimelic acid-free bacteria include bacteria such as lactic acid bacteria including *Lactobacillus delbrueckii*, *Lactobacillus acidophilus*, *Lactobacillus crispatus*, *Lactobacillus gasseri*, *Lactobacillus helveticus*, *Lactobacillus johnsonii*, *Lactobacillus kefiranofaciens*, *Lactobacillus casei*, *Lactobacillus paracasei*, *Lactobacillus coryniformis*, *Lactobacillus sakei*, *Lactobacillus brevis*, *Lactobacillus buchneri*, and the like; and bifidobacteria including *Bifidobacterium animalis*, *Bifidobacterium bifidum*, *Bifidobacterium breve*, *Bifidobacterium infantis*, *Bifidobacterium longum*, *Bifidobacterium adolescentis*, and the like. The diaminopimelic acid-free bacteria may include only one type or two or more types, but preferably include only one type. In one embodiment, the diaminopimelic acid-free bacteria are preferably lactic acid bacteria not containing diaminopimelic acid, bifidobacteria not containing diaminopimelic acid, or the like, more preferably bifidobacteria not containing diaminopimelic acid. In one embodiment, the test sample may contain diaminopimelic acid-containing bacteria and bifidobacteria and/or lactic acid bacteria not containing diaminopimelic acid (preferably, bifidobacteria or lactic acid bacteria not containing diaminopimelic acid). The diaminopimelic acid-free bacteria may be viable bacteria or dead bacteria. Use of the method of the present invention for quantification of bacteria in a test sample containing diaminopimelic acid-containing bacteria and diaminopimelic acid-free bacteria enables selective quantification of the diaminopimelic acid-containing bacteria, using, as an index, the amount of diaminopimelic acid derived from the diaminopimelic acid-containing bacteria in the test sample, regardless of whether the diaminopimelic acid-free bacteria are viable bacteria or dead bacteria.

In one embodiment, preferably, the diaminopimelic acid-containing bacteria are dead bacteria.

The bacteria quantification method of the present invention can be used as a method of quantifying dead bacteria containing diaminopimelic acid in a test sample that contains the dead bacteria containing diaminopimelic acid and diaminopimelic acid-free bacteria. The quantification method of the present invention is useful for determining the dead bacterial count containing diaminopimelic acid in a test sample that contains the dead bacteria containing diaminopimelic acid and diaminopimelic acid-free bacteria. The bacteria quantification method of the present invention is also useful as a method of quantifying dead bacteria containing diaminopimelic acid in a test sample that contains the dead bacteria containing diaminopimelic acid and viable bacteria not containing diaminopimelic acid. When the diaminopimelic acid-containing bacteria are dead bacteria, the culture method cannot be used for quantification as described above. With DAPI (fluorescent) staining, it is possible to determine the total bacterial count in a test sample that contains diaminopimelic acid-containing bacteria and diaminopimelic acid-free bacteria, but it is difficult to quantify diaminopimelic acid-containing bacteria. The bacteria quantification method of the present invention can selectively quantify diaminopimelic acid-containing bacteria in a test sample, even when the diaminopimelic acid-containing bacteria in the test sample are dead bacteria and the sample also contains diaminopimelic acid-free bacteria.

In the quantification method of the present invention, the amount of diaminopimelic acid derived from the diaminopimelic acid-containing bacteria in the test sample is used as an index to quantify the diaminopimelic acid-containing bacteria.

The quantification method of the present invention may include a step of quantifying the amount of diaminopimelic acid in the test sample. The quantification method of the present invention may be a method of quantifying bacteria, including a step of quantifying the amount of diaminopimelic acid in a test sample that contains diaminopimelic acid-containing bacteria, and a step of quantifying the diaminopimelic acid-containing bacteria, using, as an index, the amount of diaminopimelic acid derived from the diaminopimelic acid-containing bacteria in the test sample. Any method may be used to quantify the amount of diaminopimelic acid in the test sample. The amount of diaminopimelic acid in the test sample can be determined by, for example, subjecting the test sample to acid hydrolysis and quantifying the amount of diaminopimelic acid in the resulting solution. The quantification method of the present invention may include a step of subjecting the test sample to acid hydrolysis to quantify the amount of diaminopimelic acid in a resulting solution. The amount of diaminopimelic acid derived from the diaminopimelic acid-containing bacteria can be determined from the amount of diaminopimelic acid in the resulting solution. The diaminopimelic acid-containing bacteria can be quantified, using, as an index, the amount of diaminopimelic acid derived from the diaminopimelic acid-containing bacteria.

Conditions for acid hydrolysis may be any conditions in which cell walls of the diaminopimelic acid-containing bacteria can be broken down. The acid hydrolysis can be performed in an aqueous solution of an acid. The acid hydrolysis can be performed with, for example, an acid such as hydrochloric acid. Hydrochloric acid is preferred because it is easy to handle. The concentration of an acid in an aqueous solution of the acid is preferably 0.5 to 12 N, more preferably 3 to 9 N, still more preferably 5 to 7 N. In one embodiment, the acid hydrolysis temperature is preferably 70° C. to 150° C., more preferably 90° C. to 130° C., still more preferably 100° C. to 120° C. The acid hydrolysis time can be, for example, 0.5 hours or more, preferably 1 hour or more, more preferably 6 hours or more, still more preferably 8 hours or more, and can be 40 hours or less. In one embodiment, the acid hydrolysis time may be, for example, 0.5 to 40 hours, preferably 1 to 40 hours, more preferably 6 to 40 hours, still more preferably 8 to 40 hours. Any method may be used to quantify the amount of diaminopimelic acid. For example, amino acid analysis using an amino acid analyzer, a method using high performance liquid chromatography (HPLC), or a method using LC-MS can be used. In one embodiment, preferably, the diaminopimelic acid is quantified by amino acid analysis.

Preferably, the test sample does not contain diaminopimelic acid in a component other than the diaminopimelic acid-containing bacteria. When the test sample does not contain a component containing diaminopimelic acid other than the diaminopimelic acid-containing bacteria, the diaminopimelic acid in the above-mentioned resulting solution is entirely derived from the diaminopimelic acid-containing bacteria. In this case, the amount of diaminopimelic acid in the test sample can be used as the amount of diaminopimelic acid derived from the diaminopimelic acid-containing bacteria.

When the test sample contains diaminopimelic acid in a component other than the diaminopimelic acid-containing bacteria, the amount of diaminopimelic acid in the component other than the diaminopimelic acid-containing bacteria in the test sample is separately determined, and the amount of diaminopimelic acid derived from the component other than the diaminopimelic acid-containing bacteria is subtracted from the amount of diaminopimelic acid in the test sample, whereby the amount of diaminopimelic acid derived from the diaminopimelic acid-containing bacteria can be determined. The quantification method of the present invention may include a step of quantifying the amount of diaminopimelic acid in a component other than the diaminopimelic acid-containing bacteria in the test sample.

The bacterial count of the diaminopimelic acid-containing bacteria can be determined from the thus-determined amount of diaminopimelic acid derived from the diaminopimelic acid-containing bacteria. Any method may be used to determine the bacterial count of the diaminopimelic acid-containing bacteria from the amount of diaminopimelic acid. For example, a suitable method uses a calibration curve generated in advance from samples of known bacterial count for the diaminopimelic acid-containing bacteria in the test sample. Specifically, the calibration curve is generated using values obtained by subjecting samples with known bacterial count of diaminopimelic acid-containing bacteria to acid hydrolysis as described above and quantifying the amount of diaminopimelic acid derived from the diaminopimelic acid-containing bacteria in the resulting solution. Usually, the calibration curve is generated from samples that contain bacteria of known bacterial count and of the same type as that of the diaminopimelic acid-containing bacteria in the test sample. The quantification method of the present invention can determine the total bacterial count including the diaminopimelic acid-containing bacteria (total bacterial count of viable bacteria and dead bacteria) in the test sample. The quantification method of the present invention can determine the viable bacterial count when the diaminopimelic acid-containing bacteria in the test sample are entirely viable bacteria, or can determine the dead bacterial count when the bacteria are entirely dead bacteria.

The quantification method of the present invention may be a method of quantifying diaminopimelic acid-containing bacteria and diaminopimelic acid-free bacteria in a test sample. The quantification method of the present invention may include a step of quantifying the diaminopimelic acid-free bacteria in the test sample. For example, when the diaminopimelic acid-free bacteria are viable bacteria, the quantification method of the present invention may include a step of quantifying the viable bacteria not containing diaminopimelic acid in the test sample. In this case, the order of the step of quantifying the diaminopimelic acid-containing bacteria and the step of quantifying the viable bacteria not containing diaminopimelic acid is not limited.

The viable bacteria may be quantified by any method. For example, the viable bacterial count can be determined by a method such as the culture method. For example, in the step of quantifying the viable bacteria not containing diaminopimelic acid, the test sample may be cultured and colonies of the viable bacteria not containing diaminopimelic acid may be enumerated to quantify the viable bacteria. The test sample may be cultured by a method (solid culture method) that uses an agar medium for culturing.

Culturing and enumeration of viable bacterial colonies can be performed by known methods according to the type of bacteria. For example, a diluted solution of the test sample may be prepared and cultured in an agar medium, and colonies formed may be enumerated. The number of colonies formed is the viable bacterial count of bacteria in the diluted solution cultured in the agar medium. Thus, the viable bacterial count of bacteria in the test sample is determined from the number of colonies and the dilution factor.

When the diaminopimelic acid-containing bacteria are dead bacteria, culture conditions may be any conditions in which viable bacteria not containing diaminopimelic acid grow. When the test sample contains two or more types of viable bacteria, the test sample may be cultured in a selective medium or the like and the viable bacterial count of each type of bacteria may be determined. For example, when the diaminopimelic acid-containing bacteria are viable bacteria, it is possible to selectively quantify viable bacteria not containing diaminopimelic acid by, for example, using a selective medium or conditions in which the diaminopimelic acid-containing bacteria do not grow and the viable bacteria not containing diaminopimelic acid grow.

Any test sample may be used in the present invention. Examples of the test sample include foods (including health foods), pharmaceuticals, cosmetics, and raw materials of these products. The test sample may be in any form, such as a solid, a powder, a paste, a gel, a jelly, a tablet, or a liquid. If needed, the test sample can be pulverized or like for quantification of diaminopimelic acid or quantification of viable bacteria.

The quantification method of the present invention can easily quantify diaminopimelic acid-containing bacteria in products such as foods, pharmaceuticals, and cosmetics, and raw materials of these products which contain diaminopimelic acid-containing bacteria. The quantification method of the present invention can quantify diaminopimelic acid-containing bacteria in the sample, regardless of whether the bacteria are dead bacteria or viable bacteria. The quantification method of the present invention is also useful, for example, for controlling the quality of such foods, pharmaceuticals, cosmetics, raw materials of these products, and the like.

EXAMPLES

The present invention is more specifically described below with reference to examples, but the present invention is not limited to these examples.

<Diaminopimelic Acid Quantification Method>

A sample was subjected to acid hydrolysis, and the resulting solution was analyzed by automated amino acid analysis to quantify diaminopimelic acid.

(1) Analyzer and the Like
  Fully automated amino acid analyzer (JLC-500/V2, available from JEOL Ltd.)
  Analytical column (LCR-6 (5 µm, 4.0 mm i.d.×120 mm, available from JEOL Ltd.))
(2) Reagent
  2,6-Diaminopimelic acid (DAP) (Tokyo Chemical Industry Co., Ltd.)
  20% Hydrochloric acid (for precise analysis, FUJIFILM Wako Pure Chemical Corporation) (6 mol/L hydrochloric acid)
  2-Mercaptoethanol (FUJIFILM Wako Pure Chemical Corporation)
  Hydrochloric acid (for automated amino acid analysis, FUJIFILM Wako Pure Chemical Corporation)
  Trisodium citrate dihydrate (for automated amino acid analysis, FUJIFILM Wako Pure Chemical Corporation)
  Octanoic acid (n-caprylic acid) (for automated amino acid analysis, FUJIFILM Wako Pure Chemical Corporation)
  Thiodiethylene glycol (for automated amino acid analysis, FUJIFILM Wako Pure Chemical Corporation)
  Sodium citrate buffer (H-01 to H-04) (JEOL Ltd.)
  Ninhydrin Coloring Solution Kit-II for JEOL (FUJIFILM Wako Pure Chemical Corporation)
(3) Preparation of Test Solution
  20% Hydrochloric acid (containing 0.04% 2-mercaptoethanol)
  20% Hydrochloric acid (500 mL) was mixed with 2-mercaptoethanol (0.2 mL).
  Sodium citrate buffer (pH 2.2)
  Trisodium citrate dihydrate (980 g) was weighed out, and mixed with and dissolved in ion-exchanged water (about 3500 mL). The solution was mixed with 36% hydrochloric acid (about 700 mL) and octanoic acid (5 mL) and stirred. The pH was adjusted to 2.2 with 20% hydrochloric acid, and then ion-exchanged water was added to make up to 5000 mL (undiluted solution). The undiluted solution (500 mL) was mixed with thiodiethylene glycol (100 mL) and ion-exchanged water (4000 mL) and stirred. The pH was adjusted to 2.2 with 20% hydrochloric acid, and then ion-exchanged water was added to make up to 5000 mL.
  0.01 mol/L Hydrochloric acid
  Ion-exchanged water (400 mL) was mixed with 20% hydrochloric acid (80 mL) and stirred to obtain 1 mol/L hydrochloric acid, which was then diluted 100-fold with water.
(4) Preparation of Sample for Analysis
  1) A sample for analysis was placed in a test tube for hydrolysis, and mixed with 20% hydrochloric acid (containing 0.04% 2-mercaptoethanol, 20 mL). The test tube was sealed under vacuum.
  2) The sealed test tube was heated at 110° C. for 24 hours to hydrolyze the sample.
  3) After cooling, the test tube was opened, and the resulting solution of hydrolysis was made up to 100 mL with ion-exchanged water.
  4) A portion (10 mL) of the solution was separated, and concentrated and dried by an evaporator under vacuum.
  5) The resulting residue was dissolved in sodium citrate buffer (pH 2.2; 5 mL), and the resulting solution was filtered through a membrane filter (0.45 µm), whereby a test solution was obtained.
  6) DAP (0.0475 g) was precisely weighed, dissolved in 0.01 mol/L hydrochloric acid, and made up to 100 mL, whereby a standard undiluted solution was obtained (concentration: 2.5 µmol/mL).
  7) The standard undiluted solution was diluted 25-fold with sodium citrate buffer (pH 2.2), whereby a standard solution was obtained (concentration: 0.1 µmol/mL).
  8) An automated amino acid analyzer described below was used under the following conditions to quantify DAP from the peak heights in the test solution and the standard solution.
(5) Analysis by Automated Amino Acid Analyzer
  The sample prepared by the above method was analyzed under the following analysis conditions to quantify DAP.
(Analysis Conditions)
Column: LCR-6 (5 µm, 4.0 mm i.d.×120 mm, available from JEOL Ltd.)

Flow rate: 0.42 mL/min for mobile phase; 0.22 mL/min for reaction solution
Mobile phase: Sodium citrate buffer (H-01 to 04) (JEOL Ltd.)
Reaction solution: Ninhydrin Coloring Solution Kit-II for JEOL (FUJIFILM Wako Pure Chemical Corporation)
Injection volume: 30 μL Table 1 shows the percentage (vol %) of each sodium citrate buffer (H-01 to H-04) in the mobile phase and the column temperature.
(Time Program for Automated Amino Acid Analyzer)

TABLE 1

| Time (min) | Sodium citrate buffer | | | | Column temperature |
| --- | --- | --- | --- | --- | --- |
| | H-01 | H-02 | H-03 | H-04 | |
| 0:00 | 100 | 0 | 0 | 0 | 55° C. |
| 1:30 | 0 | 100 | 0 | 0 | 43° C. |
| 4:00 | 0 | 0 | 100 | 0 | 43° C. → 63° C. |
| 10:00 | 0 | 0 | 100 | 0 | 63° C. |
| 18:30 | 0 | 0 | 0 | 100 | |
| 32:00 | 0 | 0 | 0 | 100 | |

(6) Calculation Method

The amount of DAP (mg/100 g) was calculated from the following formula.

$$\text{Amount of } DAP \text{ (mg/100 g)} = 0.1 \times 190.20 \times \frac{A}{B} \times 50 \times \frac{100}{W} \times 10^{-3} \qquad [\text{Formula 1}]$$

A: Peak height of test solution
B: Peak height of standard solution
50: Dilution factor of test solution during steps 1) to 5) in (4) above
W: Amount of sample collected (g)
0.1: Concentration of standard solution (μmol/mL)
190.20: Molecular weight of DAP The peaks in A and B in the above formula are the peaks of DAP.

(7) Qualitative Confirmation

The test solution and the standard solution were analyzed by the method described in (5), and the peak corresponding to the elution retention time of the DAP standard solution was defined as DAP.

Test Example 1

The correlation between the bacterial count of *Lactobacillus pentosus* SAM 2336 (hereinafter referred to as "lactic acid bacteria S-PT84") and the amount of diaminopimelic acid (DAP) was examined. Lactic acid bacteria S-PT84 is deposited in International Patent Organism Depositary, Biotechnology Center, National Institute of Technology and Evaluation (NITE-IPOD) (accession number: FERM BP-10028), and is a strain of lactic acid bacteria identified as *Lactobacillus pentosus* SAM 2336.

Lactic acid bacteria S-PT84 was cultured, and the bacterial count of lactic acid bacteria S-PT84 and the amount of DAP in each culture time was determined.

For evaluation, sampling was performed at every three hours from hours 0 to 24. For determination of the amount of DAP, a culture solution (150 g) sampled at fixed time was sterilized and centrifuged. The supernatant was then removed, and water was added to the resulting precipitate to make up to 1.5 g to prepare a 100-fold concentrated solution as a sample for determining the amount of DAP. The amount of DAP was determined by the diaminopimelic acid quantification method. For determination of the bacterial count of lactic acid bacteria S-PT84, lactic acid bacteria S-PT84 were collected from the culture solution used for determination of the amount of DAP and stained with DAPI, and the bacterial count was then determined under a microscope. When the sample for determining the bacterial count was a 100-fold concentrated solution, the bacteria aggregated, which interfered with accurate determination of the bacterial count. Thus, the result determined from the culture solution was multiplied by 100 to obtain a value as the bacterial count. Based on these results, the correlation between the amount of DAP and the bacterial count of lactic acid bacteria S-PT84 was examined.

Figure 2:
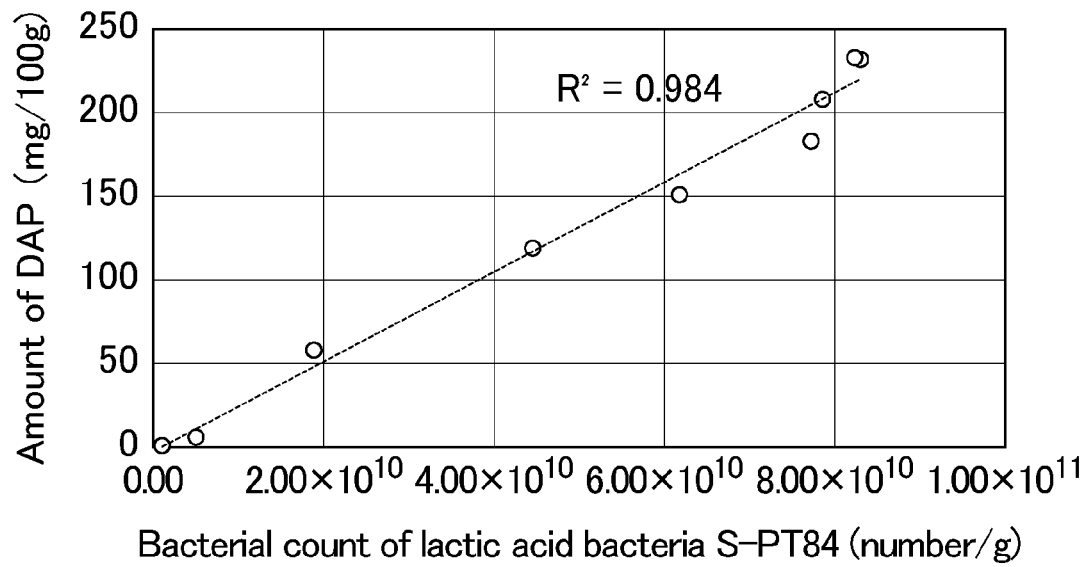
FIG. 2 is a graph showing the correlation between the bacterial count of lactic acid bacteria S-PT84 (number/g) on the vertical axis in FIG. 1A and the amount of diaminopimelic acid (mg/100 g) on the vertical axis in FIG. 1B.

FIG. 1A is a graph showing culture time-dependent changes in the bacterial count of lactic acid bacteria S-PT84. FIG. 1B is a graph showing culture time-dependent changes in the amount of diaminopimelic acid. In FIG. 1A, the bacterial count of lactic acid bacteria on the vertical axis is a value converted to the bacterial count of lactic acid bacteria S-PT84 in a 100-fold concentrated solution by multiplying the bacterial count of lactic acid bacteria S-PT84 per gram of the culture medium by 100. In FIG. 1B, the amount of DAP (mg) on the vertical axis is a value per 100 g of the 100-fold concentrated solution. FIG. 2 is a graph showing the correlation between the bacterial count of lactic acid bacteria S-PT84 (number/g) on the vertical axis in FIG. 1A and the amount of diaminopimelic acid (mg/100 g) on the vertical axis in FIG. 1B. As shown in FIG. 1A, the bacterial count of lactic acid bacteria S-PT84 started to increase at hour 3, and no changes in the bacterial count were observed at hour 21 and thereafter. The amount of DAP also showed a similar tendency (FIG. 1B). Further, the results of the bacterial count of lactic acid bacteria S-PT84 and the amount of DAP were plotted. The correlation was checked based on an approximate straight line, and a high correlation was confirmed, with the value of $R^2$ being 0.984 (FIG. 2).

Test Example 2

To check the correlation between the weight of lactic acid bacteria S-PT84 raw material and the amount of DAP, DAP per weight of lactic acid bacteria S-PT84 raw material was quantified by the diaminopimelic acid quantification method. The test was repeated once daily for three days.

Lactic acid bacteria S-PT84 raw material were dead lactic acid bacteria S-PT84 powder (containing $1.8 \times 10^{11}$ dead bacteria per gram, available from Taiyo Corporation). The dead bacterial count is a value determined by the raw material manufacturer.

Figure 3:
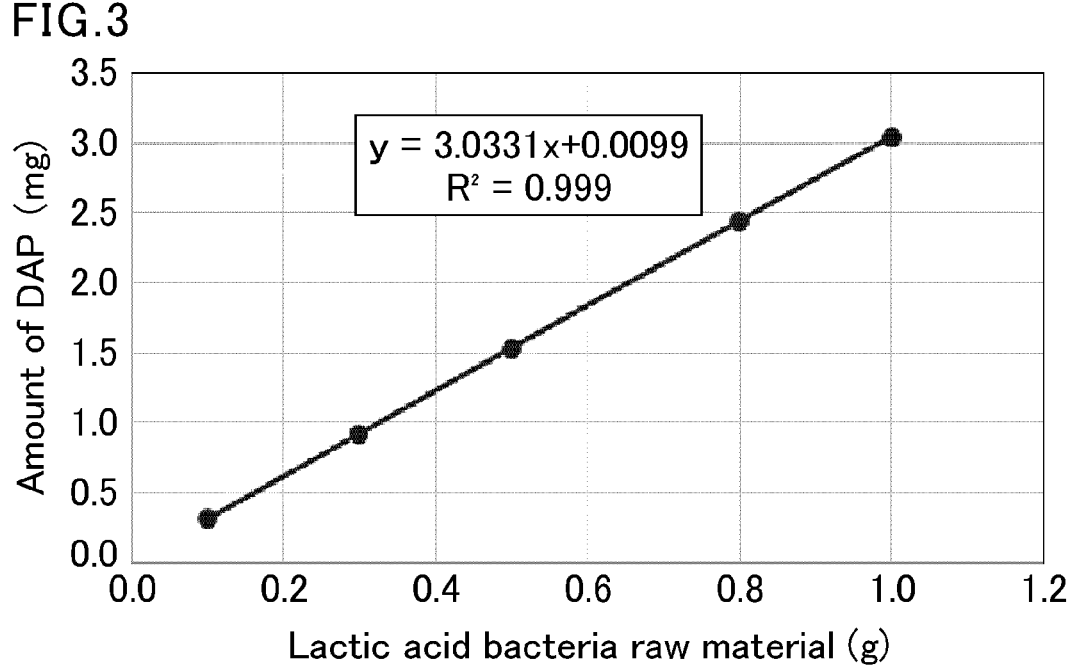
FIG. 3 is a graph showing the correlation between the weight of lactic acid bacteria S-PT84 raw material and the amount of diaminopimelic acid in the raw material.

Table 2 shows measured values and analysis results of DAP per weight of lactic acid bacteria S-PT84 raw material. FIG. 3 shows a graph plotting the results shown in Table 2 (horizontal axis: amount of specimen (lactic acid bacteria raw material) (g); vertical axis: average analysis results (amount of DAP) (mg)). The graph in FIG. 3 shows the correlation between the weight of lactic acid bacteria S-PT84 raw material and the amount of DAP in the raw material.

The linearity between the weight of lactic acid bacteria S-PT84 raw material and the amount of DAP checked was checked, and a high linearity was confirmed, with the value of $R^2$ being 0.999 (Table 2 and FIG. 3). A regression equation determined from the data in the FIG. 3 was as follows: y=3.0331x+0.0099.

TABLE 2

| Amount of specimen (g) (lactic acid bacteria S-PT84 raw material) | Measured values (mg) | | | Average analysis results (mg) |
|---|---|---|---|---|
| | Day 1 | Day 2 | Day 3 | |
| 0.1 | 0.3091 | 0.3133 | 0.3097 | 0.3107 |
| 0.3 | 0.9074 | 0.9313 | 0.9205 | 0.9197 |
| 0.5 | 1.5242 | 1.5385 | 1.5223 | 1.5283 |
| 0.8 | 2.4550 | 2.4578 | 2.4151 | 2.4426 |
| 1.0 | 3.0393 | 3.0407 | 3.0314 | 3.0371 |

In Test Example 1, the correlation between the bacterial count of lactic acid bacteria S-PT84 and the amount of DAP in each culture time was evaluated. Based on an approximate straight line between the bacterial count of lactic acid bacteria S-PT84 and the amount of DAP, a high correlation was confirmed, with the value of $R^2$ being 0.984. Since DAP is present in cell walls of lactic acid bacteria S-PT84, presumably, the amount of DAP increased with proliferation of lactic acid bacteria S-PT84. In Test Example 2, the correlation between the weight of lactic acid bacteria S-PT84 raw material and the amount of DAP was examined, and a high linearity was demonstrated, with the value of $R^2$ being 0.999. This shows that the measurement of the amount of DAP enables calculation of the bacterial count of DAP-containing bacteria and the amount of the bacteria raw material.

In addition, the correlation between the bacterial count of lactic acid bacteria S-PT84 and the amount of DAP was evaluated as in the diaminopimelic acid quantification method, except that the acid hydrolysis time was changed to 8, 16, 32, or 40 hours in step 2) in "(4) Preparation of sample for analysis". Even when the hydrolysis time was changed to 8, 16, 32, or 40 hours, the result was the same as that obtained with the hydrolysis time of 24 hours. This confirmed sufficient hydrolysis of lactic acid bacteria S-PT84 raw material.

Example 1

Lactic acid bacteria S-PT84 raw material were the dead lactic acid bacteria S-PT84 powder (a product containing $1.8 \cdot 10^{11}$ dead bacteria per gram, available from Taiyo Corporation) as in Test Example 2.

The DAP-free bacteria were bifidobacteria. The lactic acid bacteria S-PT84 raw material and bifidobacteria raw material were mixed to prepare a sample containing $4.1 \times 10^{12}$ lactic acid bacteria S-PT84 (dead bacteria) per 100 g.

The amount of DAP in the sample was quantified by the diaminopimelic acid quantification method. In addition, a calibration curve was generated by the following method, and the bacterial count of lactic acid bacteria S-PT84 was determined from the amount of DAP in the sample.
(Generation of Calibration Curve)

Lactic acid bacteria S-PT84 raw material used to prepare the sample was weighed out in an amount of 0.1, 0.3, 0.5, 0.8, or 1.0 g. DAP was quantified according to the procedure described in (4) to (7) of the diaminopimelic acid quantification method, and a regression line was generated from measurements of the amount of DAP and the amount of lactic acid bacteria S-PT84 raw material. This regression line was used as a calibration curve. Changes were made to 5) in (4) of the diaminopimelic acid quantification method as described in 5') below.

5') The resulting residue was dissolved in sodium citrate buffer (pH 2.2; 20 mL), and the residue solution was filtered through a membrane filter (0.45 µm), whereby a test solution was obtained.
(Conversion of Bacterial Count of Lactic Acid Bacteria S-PT84)

Using the slope and intercept of the calibration curve (regression line) generated above, the amount of lactic acid bacteria S-PT84 raw material per 100 g of the sample was calculated as below.

(Amount of lactic acid bacteria S-PT84 raw material per 100 g of sample(g/100 g)=(E−intercept)/slope E: Amount of DAP (mg/100 g)
The following formula was used to convert the amount of lactic acid bacteria S-PT84 raw material per 100 g of the sample to the bacterial count of lactic acid bacteria S-PT84 per 100 g of the sample.
Bacterial count of lactic acid bacteria S-PT84 per 100 g of sample (number/100 g)=M×T
M: Amount of lactic acid bacteria S-PT84 raw material per 100 g of sample (g/100 g)
T: Bacterial count per amount of lactic acid bacteria S-PT84 raw material (number/g)
(The bacterial count (number/g) is the bacterial count (dead bacteria) of lactic acid bacteria S-PT84 (number/g), and is a value determined by the raw material manufacturer.)

The bacterial count of lactic acid bacteria S-PT84 per 100 g of the sample was $4.2 \times 10^{12}$/100 g, as determined by the above method.

The sample prepared in Example 1 contained bifidobacteria raw material in addition to lactic acid bacteria S-PT84. The amount of DAP in the bifidobacteria raw material was checked. As a result, no DAP was detected from the bifidobacteria raw material.

Lactic acid bacteria S-PT84 raw material is obtained as the raw material by culturing the bacteria in a medium (containing yeast extract and glucose), separating the bacteria by solid-liquid separation, freeze drying the resulting precipitate, and pulverizing the freeze-dried product. Since the raw material might have been mixed with the medium, the amount of DAP in the raw materials of the medium for the lactic acid bacteria S-PT84 was checked. As a result, no DAP was detected from any of the specimens. Based on the above results, DAP detected from the sample in Example 1 was considered to be entirely derived from lactic acid bacteria S-PT84.

The above results show that it is possible to determine the bacterial count of the DAP-containing bacteria, using the amount of DAP as an index.

Example 2

The DAP-free bacteria were *Bifidobacterium bifidum* (*B. bifidum*) strain NBRC 100015 of bifidobacteria (hereinafter "bifidobacteria NBRC 100015"). Bifidobacteria NBRC 100015 are available from Biotechnology Center, National Institute of Technology and Evaluation (NBRC No. NBRC 100015). To mix bifidobacteria NBRC 100015 with lactic acid bacteria S-PT84 raw material, skim milk powder was added to a culture medium of bifidobacteria NBRC 100015 to prepare powdered bifidobacteria NBRC 100015 as a raw material (a product containing $3.4 \times 10^{10}$ viable bacteria per gram). The viable bacterial count of bifidobacteria NBRC 100015 raw material is a value determined by Japan Food Research Laboratories. Lactic acid bacteria S-PT84 raw material were the dead lactic acid bacteria S-PT84 powder (a product containing $1.8 \times 10^{11}$ dead bacteria per gram, available from Taiyo Corporation) as in Test Example 2.

Lactic acid bacteria S-PT84 raw material and bifidobacteria NBRC 100015 raw material were mixed to prepare a sample containing $4.1 \times 10^{12}$ lactic acid bacteria S-PT84 (dead bacteria) and $2.6 \times 10^{12}$ bifidobacteria NBRC 100015 (viable bacteria) per 100 g.

The amount of DAP in the sample was quantified by the diaminopimelic acid quantification method. A calibration curve was generated from the amount of DAP and the amount of lactic acid bacteria S-PT84 raw material as in Example 1, and the bacterial count of lactic acid bacteria S-PT84 was determined from the amount of DAP in the sample.

The bacterial count of lactic acid bacteria S-PT84 was determined from the amount of DAP. The bacterial count of lactic acid bacteria S-PT84 in the sample was $4.5 \times 10^{12}/100$ g. The amount of DAP in bifidobacteria NBRC 100015 raw material used was checked. As a result, no DAP was detected from the raw material.

The viable bacterial count of bifidobacteria NBRC 100015 in the sample was determined by a method of culturing the sample in an agar medium and then enumerating colonies (culture method). The viable bacterial count of bifidobacteria NBRC 100015 in the sample was $2.0 \times 10^{12}/100$ g.

Example 3

The DAP-free bacteria were *Lactobacillus acidophilus* (*L. acidophilus*) strain NBRC 13951 of lactic acid bacteria (hereinafter "lactic acid bacteria NBRC 13951"). Lactic acid bacteria NBRC 13951 are available from Biotechnology Center, National Institute of Technology and Evaluation (NBRC No. NBRC 13951). To mix lactic acid bacteria NBRC 13951 with lactic acid bacteria S-PT84 raw material, skim milk powder was added to a culture medium of lactic acid bacteria NBRC 13951 to prepare powdered lactic acid bacteria NBRC 13951 as a raw material (a product containing $1.0 \times 10^8$ viable bacteria per gram). The viable bacterial count of lactic acid bacteria NBRC 13951 raw material is a value determined by Japan Food Research Laboratories.

Lactic acid bacteria S-PT84 raw material were the dead lactic acid bacteria S-PT84 powder (a product containing $1.8 \times 10^{11}$ number/g of dead bacteria, available from Taiyo Corporation) as in Test Example 2.

Lactic acid bacteria S-PT84 raw material and lactic acid bacteria NBRC 13951 raw material were mixed to prepare a sample containing $4.1 \times 10^{12}$ lactic acid bacteria S-PT84 (dead bacteria) and $7.7 \times 10^9$ lactic acid bacteria NBRC 13951 (viable bacteria) per 100 g.

The amount of DAP in the sample was quantified by the diaminopimelic acid quantification method. A calibration curve was generated from measurements of the amount of DAP and the amount of lactic acid bacteria S-PT84 raw material as in Example 1, and the bacterial count of lactic acid bacteria S-PT84 was determined from the amount of DAP in the sample.

The bacterial count of lactic acid bacteria S-PT84 was determined from the amount of DAP. The bacterial count of lactic acid bacteria S-PT84 in the sample was $4.7 \times 10^{12}/100$ g. The amount of DAP in lactic acid bacteria NBRC 13951 raw material used was checked. As a result, no DAP was detected from the raw material.

The viable bacterial count of lactic acid bacteria NBRC 13951 in the sample was determined by a method of culturing the sample in an agar medium and then enumerating colonies (culture method). The viable bacterial count of lactic acid bacteria NBRC 13951 in the sample was $7.4 \times 10^9/100$ g.

According to "III. Quality Control in Microbiological Testing" in "General Guidelines for Quality Control" for "Practice of Inspection Task Control in Food Sanitation Inspection Facilities" (Apr. 1, 1997) (Ei-Shoku No. 117), the recovery rate of known microorganisms added is required to be at least 70% to 120% ("(1) Requirements for recovery rate and the like" in "2. Setting target values required for quality control"). In lactic acid bacteria S-PT84 in Examples 1 to 3 and bifidobacteria NBRC 100015 and lactic acid bacteria NBRC 13951 in Examples 2 and 3, the determined bacterial count in the sample relative to the bacterial count (calculated value) in the sample calculated from the quantitative value of each raw material is in the above range. Thus, the quantification method of the present invention is considered to provide sufficient accuracy for quantification of bacteria.

The invention claimed is:

1. A method of determining a bacterial count of diaminopimelic acid-containing bacteria in a test sample containing diaminopimelic acid-containing bacteria and diaminopimelic acid-free bacteria, comprising:
   a step of determining a bacterial count of the diaminopimelic acid-containing bacteria, using, as an index, an amount of diaminopimelic acid derived from the diaminopimelic acid-containing bacteria in the test sample,
   wherein the test sample is a food, a pharmaceutical, a cosmetic, or a raw material of any of these products.

2. The method according to claim 1,
   wherein the diaminopimelic acid-containing bacteria are dead bacteria.

3. The method according to claim 1,
   wherein the diaminopimelic acid-containing bacteria include at least one type of lactic acid bacteria selected from the group consisting of *Lactobacillus pentosus*, *Lactobacias plantarum*, *Lactobacillus paraplantarum*, *Lactobacillus fabifermentans*, *Lactobacillus vaccinostercus*, *Lactobacillus hokkaidonensis*, *Lactobacillus oligolernientans*, *Lactobacillus suebicus*, *Lactobacillus mali*, and *Lactobacillus divergens*.

4. The method according to claim 1,
   wherein the diaminopimelic acid-containing bacteria are of *Lactobacillus pentosus*.

5. The method according to claim 1,
   wherein the diaminopimelic acid-containing bacteria include only one type of dead bacteria,
   the diaminopimelic acid-containing bacteria are of *Lactobacillus pentosus*, and the diaminopimelic acid-free bacteria are viable bacteria.

* * * * *